United States Patent [19]

Novick

[11] Patent Number: 5,035,001

[45] Date of Patent: Jul. 30, 1991

[54] HOT SLEEVE, AND METHODS OF CONSTRUCTING AND UTILIZING SAME

[76] Inventor: Carl A. Novick, 4653 Raymond, Dearborn Heights, Mich. 48125

[21] Appl. No.: 580,090

[22] Filed: Sep. 10, 1990

[51] Int. Cl.$^5$ ............................................. A41D 13/08
[52] U.S. Cl. ............................................. 2/125; 2/16; 2/59; 2/102
[58] Field of Search ...................... 2/16, 46, 59, 90, 91, 2/94, 102, 108, 125, 126

[56] References Cited

U.S. PATENT DOCUMENTS

| | | | |
|---|---|---|---|
| 1,561,400 | 11/1925 | Begg | 2/126 X |
| 2,677,131 | 5/1954 | Shuster | 2/126 |
| 3,024,466 | 3/1962 | Agostini | . |
| 4,302,850 | 12/1981 | Maeshima | . |
| 4,356,570 | 11/1982 | Vernon et al. | . |
| 4,569,087 | 2/1986 | Kerwin | . |
| 4,951,317 | 8/1990 | Gray et al. | . |
| 4,985,935 | 1/1991 | Perry | 2/59 X |

FOREIGN PATENT DOCUMENTS 3105119  9/1982  Fed. Rep. of Germany ............ 2/46

Primary Examiner—Werner H. Schroeder
Assistant Examiner—Jeanette E. Chapman
Attorney, Agent, or Firm—Irving M. Weiner; Robert M. Petrik; Joseph P. Carrier

[57] ABSTRACT

The garment for use by athlete for retaining body heat adjacent to the arm and shoulder muscles and the major muscles utilized while throwing an object. The throwing motion utilizes the upper back and torso muscles in addition to the shoulder and arm muscles. Thus, it is desirable to retain body heat on these muscles to prevent them from "tightening up" while the athlete is idle, such as between innings of a baseball game.

3 Claims, 1 Drawing Sheet

HOT SLEEVE, AND METHODS OF CONSTRUCTING AND UTILIZING SAME

BACKGROUND OF THE INVENTION

1. Field of the Invention

The present invention relates to garments worn by athletes. More particularly, the invention relates to a supplemental garment for covering one arm and torso of an athlete for maintaining body heat in the upper torso muscles.

2. Description of the Relevant Art

It is well known that it is important for athletes to "warm up" before fully exercising the muscles while conditioning or when performing athletics. Failure to do so may result in injuries in the muscles, such as muscle tears or muscle strains.

It is also important for the athlete to remain "warm" while waiting to perform. Various types of sweat suits and jackets are well known for this purpose.

For example, U.S. Pat. No. 4,356,570 discloses a sleeve to be worn over a players arm and shoulder. The sleeve attaches to the uniform by VELCRO fasteners. This garment is only designed to keep the arm warm while other muscles in the back and torso cool down.

U.S. Pat. No. 3,024,466 discloses a protective garment for use while handling a baby while burping. The garment is primarily a bib and does not surround the entire torso.

U.S. Pat. No. 4,569,087 discloses a sleeve garment for use in retaining warmth and for applying a cooling medium to the arm. The garment covers only the arm or comprises an entire jacket or pants. The sleeves or pants leg includes a compartment for the cooling medium to be held adjacent the selected limb.

U.S. Pat. No. 4,302,850 discloses a vest convertible to a jacket with sleeves. The vest has an opening in the shoulder area to accept the folded sleeve for storage.

SUMMARY OF THE INVENTION

The present invention provides a garment for an athlete, particularly an athlete that throws a ball or other object. The garment provides thermal protection for the major muscle groups used in the throwing motion including the arm, back and torso muscles. The throwing motion requires a significant amount of twisting and elongation of muscles, and thus it is imperative that these muscles are properly "warmed up" and "loosened" to prevent injury. Once this is accomplished, it is imperative that the muscles not be permitted to "tighten up".

The garment is securely worn by the athlete with no possibility of the sleeve accidently falling off. The arm and shoulder area (of the garment) comprises two layers of material while the torso portion comprises only one layer of material.

It is an object of the present invention to provide a garment with thermal protection of an arm and upper torso.

It is a further objective of the present invention to provide a garment which is worn by an athlete without the possibility of falling off.

it is a still further object of the present invention to provide a garment with increased thermal protection to the arm and shoulder and somewhat lower thermal protection to the torso of the where.

The above and further objects, details and advantages of the invention will become apparent from the following detailed description, when read in conjunction with the accompanying drawings.

DETAILED DESCRIPTION OF THE PREFERRED EMBODIMENTS

Figure 1:
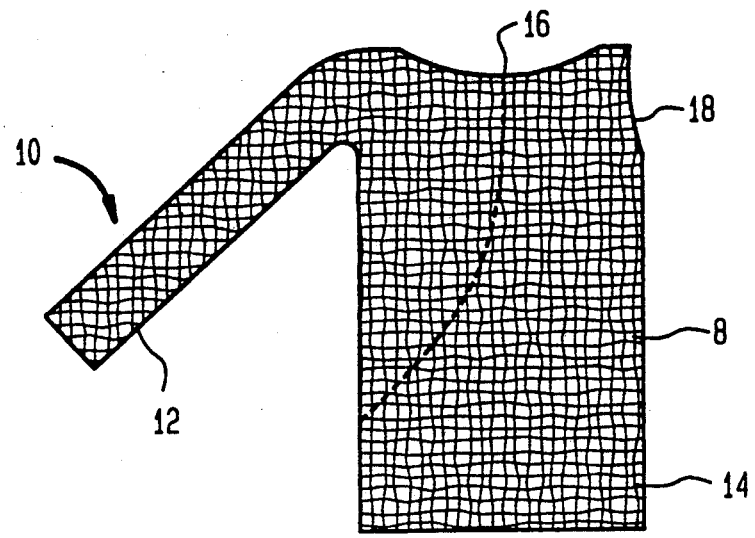
FIG. 1 illustrates a garment in accordance with the present invention.

As shown in FIG. 1, the garment 10 comprises a sleeve 12 and torso encircling means 14 preferably comprising 46% cotton, 46% polyester and 8% lycra adapted to be worn under the normal uniform of the athlete. Torso encircling means 14 includes neck opening 16 and sleeveless arm opening 18.

The sleeve 12 is generally tubular with a first open end at the wrist and a second end attached to the torso encircling means 14 at the shoulder opposite sleeve arm opening 18. Sleeve 12 should be provided approximately in length equivalent to length of the wear's arm and can be provided for a left or right handed person. The torso and circular means 14 is also generally tubular with the opening as described above.

Figure 2:
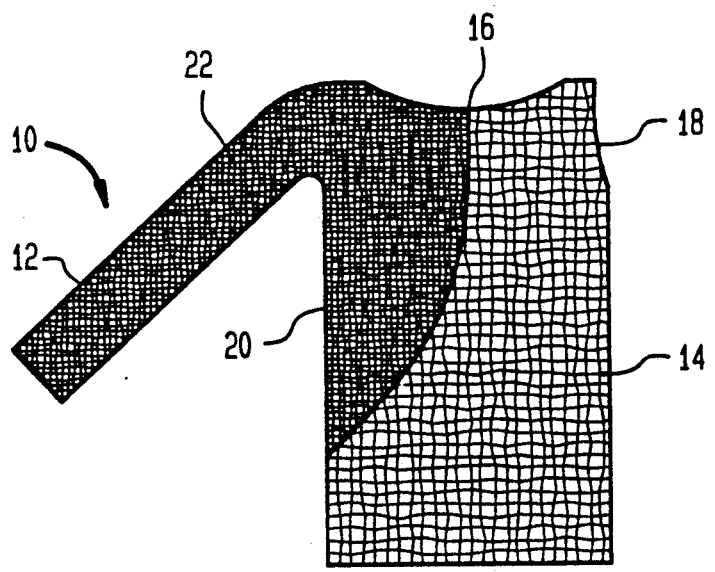
FIG. 2 illustrates an inside out view of the garment in accordance with the present invention.

Sleeve 12 and the shoulder portion 20 adjacent thereto, include a second layer of insulative material as best seen in FIG. 2 preferably comprising 100% interlocking cotton. This second layer 22 aids in retaining the warmth or body heat radiated therefrom adjacent the arm and shoulder. The portion 20 extends substantially in a semi-circular shape from the sleeve 12 and extends more than half-way down the torso encircling means 14 and substantially half-way across neck opening 16. The size of portion 20 prevents the muscles of the back and shoulder, in addition to the arm muscles, from "stiffening" or cooling while the athlete is idle, such as between innings in a baseball game. The remaining portion of torso encircling means 14 retaining less body heat that the portion including second layer 22.

However, portion 14 permits the major muscles groups required in the throwing motion to remain warm or "loose".

Since torso encircling means 14 allows the wearer to move about without fear of the sleeve falling off, the garment of the present invention may even be worn while "warming up" to hasten the pace of the muscle warming.

Whereas the garment of the present invention is envisioned as primarily used by baseball pitchers, other athletes who utilize a throwing motion may also achieve benefits by using the garment of the present invention.

The outer layer 8 and insulation layer 22 may comprise any known insulating type material. It may be desirable to provide the garment with a water repellant layer. In addition, the garment 10 may be provided with an opening (not shown) in the front including fastening means, such as snaps, for securing the garment 10 on the athlete.

Although there has been described what is at present considered to be preferred embodiments of the invention, it will be understood that various modifications and variations may be made therein, and it is intended to cover in the appended claims all such modifications as full within true spirit and scope of the invention.

I claim:

1. A garment to be worn by athletes for retaining a substantial amount of body heat to maintain the temperature of the muscles needed by the athlete for throwing an object, comprising:

a torso encircling member comprising a first material layer including a first aperture for accommodating the passage of an athletes head and a second aperture to accommodate the passage of an arm which is not used for throwing;

a sleeve member secured to said torso encircling member adapted to cover an arm used for throwing; and a second layer of material provided on said sleeve member and the portion of said torso encircling member adjacent said sleeve member.

2. The garment of claim 1 wherein:
said sleeve member and said torso encircling member are a tubular shape.

3. The garment of claim 2, wherein:
said second layer of material extends substantially halfway across said neck opening and substantially halfway along the length of said torso encircling member so as to cover and retain warmth on the major muscles groups associated with throwing an object.

* * * * *

UNITED STATES PATENT AND TRADEMARK OFFICE
CERTIFICATE OF CORRECTION

PATENT NO. : 5,035,001

DATED : July 30, 1991

INVENTOR(S) : Carl A. Novick

It is certified that error appears in the above-identified patent and that said Letters Patent is hereby corrected as shown below:

Column 1, line 63, change "it" to --It--.

Signed and Sealed this

Twenty-fourth Day of November, 1992

Attest:

DOUGLAS B. COMER

Attesting Officer     Acting Commissioner of Patents and Trademarks